(12) United States Patent
Resconi et al.

(10) Patent No.: US 7,589,160 B2
(45) Date of Patent: Sep. 15, 2009

(54) PROCESS FOR PREPARING 1-BUTENE POLYMERS

(75) Inventors: Luigi Resconi, Ferrara (IT); Antonio Cascio Ingurgio, Palermo (IT)

(73) Assignee: Basell Polyolefine GmbH, Wesseling (DE)

(*) Notice: Subject to any disclaimer, the term of this patent is extended or adjusted under 35 U.S.C. 154(b) by 0 days.

(21) Appl. No.: 10/536,858

(22) PCT Filed: Nov. 3, 2003

(86) PCT No.: PCT/EP03/12236

§ 371 (c)(1),
(2), (4) Date: May 27, 2005

(87) PCT Pub. No.: WO2004/050724

PCT Pub. Date: Jun. 17, 2004

(65) Prior Publication Data

US 2006/0052553 A1    Mar. 9, 2006

Related U.S. Application Data

(60) Provisional application No. 60/431,803, filed on Dec. 9, 2002.

(30) Foreign Application Priority Data

Dec. 4, 2002  (EP) .................................. 02080120

(51) Int. Cl.
- C08F 4/64 (2006.01)
- C08F 4/72 (2006.01)
- C07F 17/00 (2006.01)

(52) U.S. Cl. ................ 526/160; 526/170; 526/943; 526/126; 526/348.6; 526/129; 526/941; 556/53; 502/103

(58) Field of Classification Search ................ 526/160, 526/170, 127, 943, 348.6; 556/53
See application file for complete search history.

(56) References Cited

U.S. PATENT DOCUMENTS

| | | | |
|---|---|---|---|
| 4,298,722 A | 11/1981 | Collette et al. | |
| 4,971,936 A * | 11/1990 | Wilson et al. | 502/124 |
| 5,132,381 A | 7/1992 | Winter et al. | |
| 5,145,819 A | 9/1992 | Winter et al. | 502/117 |
| 5,276,208 A | 1/1994 | Winter et al. | |
| 5,455,366 A * | 10/1995 | Rohrmann et al. | 556/8 |
| 5,532,396 A | 7/1996 | Winter et al. | |
| 5,576,260 A | 11/1996 | Winter et al. | |
| 5,612,428 A | 3/1997 | Winter et al. | |
| 5,616,747 A | 4/1997 | Rohrmann et al. | |
| 5,696,045 A | 12/1997 | Winter et al. | |
| 5,698,487 A | 12/1997 | Sacchetti et al. | |
| 5,700,886 A | 12/1997 | Winter et al. | |
| 5,786,432 A | 7/1998 | Kuber et al. | 526/127 |
| 5,830,821 A | 11/1998 | Rohrmann et al. | |
| 5,859,159 A | 1/1999 | Rossi et al. | 526/176 |
| 5,965,756 A * | 10/1999 | McAdon et al. | 556/11 |
| 6,034,022 A * | 3/2000 | McAdon et al. | 502/103 |
| 6,084,115 A * | 7/2000 | Chen et al. | 556/22 |
| 6,124,231 A * | 9/2000 | Fritze et al. | 502/152 |
| 6,143,827 A * | 11/2000 | Morizono et al. | 525/192 |
| 6,150,481 A | 11/2000 | Winter et al. | |
| 6,156,844 A * | 12/2000 | Hashimoto et al. | 525/240 |
| RE37,384 E | 9/2001 | Winter et al. | |
| 6,329,479 B1 * | 12/2001 | Arai et al. | 526/170 |
| 6,369,254 B1 * | 4/2002 | Resconi et al. | 556/11 |

(Continued)

FOREIGN PATENT DOCUMENTS

DE      19917985      10/2000

(Continued)

OTHER PUBLICATIONS

Halterman et al. J. Organomet. Chem. 1998, 568, 41-51.*

(Continued)

*Primary Examiner*—David Wu
*Assistant Examiner*—Rip A. Lee
(74) *Attorney, Agent, or Firm*—William R Reid

(57) ABSTRACT

A process for obtaining 1-butene polymers comprising the step of contacting under polymerization conditions 1-butene and optionally ethylene, propylene or said alpha-olefin, in the presence of a catalyst system obtainable by contacting: a) a metallocene compound of formula (I):

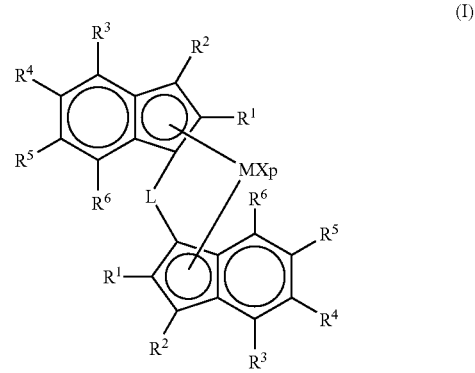

wherein: M is an atom of a transition metal belonging to group 3, 4, 5, 6 or to the lanthanide or actinide groups in the Periodic Table of the Elements; p is an integer from 0 to 3; X is a hydrogen atom, a halogen atom, or a hydrocarbon group; $R^1$ is a hydrocarbon group; $R^2$, $R^3$ and $R^6$ are hydrogen atoms or hydrocarbon groups; $R^4$ and $R^5$ join to form a condensed saturated or unsaturated 4–7 membered ring; and L is a divalent bridging group; and b) an alumoxane or a compound able to form an alkylmetallocene cation.

11 Claims, No Drawings

U.S. PATENT DOCUMENTS

| | | | |
|---|---|---|---|
| 6,399,533 | B2 | 6/2002 | Sacchetti et al. |
| 6,444,833 | B1 | 9/2002 | Ewen et al. |
| 6,448,350 | B1 | 9/2002 | Dall'Occo et al. |
| 6,451,938 | B1 | 9/2002 | Fisher et al. |
| 6,469,113 | B1 | 10/2002 | Lee et al. |
| 6,469,114 | B1 | 10/2002 | Schottek et al. |
| 6,479,424 | B1 * | 11/2002 | Ernst et al. .................. 502/152 |
| 6,482,902 | B1 | 11/2002 | Bohnen et al. |
| 6,573,352 | B1 * | 6/2003 | Tatsumi et al. .............. 526/351 |
| 6,635,779 | B1 | 10/2003 | Ewen et al. .................... 556/11 |
| 6,930,160 | B2 | 8/2005 | Minami et al. ........... 526/348.6 |
| 6,987,196 | B2 | 1/2006 | Resconi et al. |
| 7,074,864 | B2 | 7/2006 | Resconi ....................... 526/160 |
| 7,115,761 | B2 | 10/2006 | Resconi et al. |
| 7,166,683 | B2 | 1/2007 | Resconi |
| 7,241,903 | B2 | 7/2007 | Fritze et al. |
| 2003/0008984 | A1 | 1/2003 | Kratzet et al. ................ 526/127 |
| 2003/0013913 | A1 | 1/2003 | Schottek et al. ................. 564/8 |
| 2003/0149199 | A1 | 8/2003 | Schottek et al. |
| 2004/0132612 | A1 | 7/2004 | Resconi et al. |
| 2004/0242815 | A1 | 12/2004 | Resconi |
| 2004/0254315 | A1 | 12/2004 | Resconi |
| 2006/0084769 | A1 | 4/2006 | Resconi et al. .............. 526/127 |
| 2006/0155071 | A1 | 7/2006 | Morini et al. |
| 2006/0167195 | A1 | 7/2006 | Resconi et al. |

FOREIGN PATENT DOCUMENTS

| | | |
|---|---|---|
| DE | 19962814 | 6/2001 |
| DE | 19962910 | 7/2001 |
| EP | 0172961 | 3/1986 |
| EP | 186287 | 7/1986 |
| EP | 352362 | 1/1990 |
| EP | 353318 | 2/1990 |
| EP | 485823 | 5/1992 |
| EP | 0549900 | 7/1993 |
| EP | 0633272 | 1/1995 |
| EP | 775707 | 5/1997 |
| EP | 982328 | 3/2000 |
| EP | 1260525 | 11/2002 |
| GB | 1460795 | 1/1977 |
| JP | 60262804 | 12/1985 |
| JP | 62119213 | 5/1987 |
| JP | 03126704 | 5/1991 |
| WO | 9102012 | 2/1991 |
| WO | 9200333 | 1/1992 |
| WO | 92/05208 | 4/1992 |
| WO | 9532995 | 12/1995 |
| WO | 98/22486 | 5/1998 |
| WO | WO98/55520 A1 * | 12/1998 |
| WO | 9921899 | 5/1999 |
| WO | 99/40129 | 8/1999 |
| WO | 9945043 | 9/1999 |
| WO | 9946270 | 9/1999 |
| WO | 0121674 | 3/2001 |
| WO | 01/44318 | 6/2001 |
| WO | 0144319 | 6/2001 |
| WO | 0162764 | 8/2001 |
| WO | 02/16450 | 2/2002 |
| WO | 02/100909 | 12/2002 |
| WO | 02100908 | 12/2002 |
| WO | 03/042258 | 5/2003 |
| WO | 2004/033510 | 4/2004 |
| WO | 2004/048424 | 6/2004 |
| WO | 2004/050713 | 6/2004 |
| WO | 2004/050724 | 6/2004 |

OTHER PUBLICATIONS

A. Rossi et al., "End Groups in 1-Butene Polymerization via Methylaluminoxane and Zirconocene Catalyst," *Macromolecules*, vol. 28(6), p. 1739-1749 (1995).

N. Naga et al., "Effect of co-catalyst system on α-olefin polymerization with *rac*-and *meso*-[dimethylsilylenebis(2,3,5-trimethyl-cyclopentadienyl)]zirconium dichloride," *Macromol. Rapid Commun.*, vol. 18, p. 581-589 (1997).

J. Suhm et al., "Influence of metallocene structures on ethene copolymerization with 1-butene and 1-octene," *Journal of Molecular Catalysis A: Chemical*, vol. 128, p. 215-227 (1998).

Busico et al., "Regiospecificity of 1-butene polymerization catalyzed by $C_2$-symmetric group IV metallocenes," *Macromol. Rapid Commun.*, vol. 16, pp. 269-274 (1995).

Carman et al., "Monomer Sequence Distribution in Ethylene-Propylene Rubber Measured by $^{13}C$ NMR 3. Use of Reaction Probability Model," *Macromolecules*, vol. 10(3), pp. 536-544 (1977).

Office Action from currently pending U.S. Appl. No. 10/536,857 with mail date Oct. 4, 2007.

Office Action from currently pending U.S. Appl. No. 10/480,762 with mail date Dec. 20, 2007.

Amendment from currently pending U.S. Appl. No. 10/536,857 with mail date Mar. 28, 2008.

U.S. Appl. No. 11/376,409, filed Mar. 15, 2006, Resconi.

J. Ewen et al., "Polymerization Catalysts with Cyclopentadienyl Ligands Ring-Fused to Pyrrole and Thiophene Heterocycles," *J. Am. Chem. Soc.*, vol. 120(41), pp. 10786-10787 (1998).

M. Vathauer et al., "Homopolymerizations of α-Olefins with Diastereomeric Metallocene/MAO Catalysts," Macromolecules, vol. 33(6), pp. 1955-1959 (2000).

N. Naga et al., "Polymerization behavior of α-olefins with *rac*- and *meso*-type *ansa*-metallocene catalysts: Effects of cocatalyst and metallocene ligand," *Macromol. Chem. Phys.*, vol. 200, pp. 1587-1594 (1999).

Office Action from currently pending U.S. Appl. No. 10/480,762 with mail date Mar. 21, 2005.

Amendment & Response to Restriction Requirement from currently pending U.S. Appl. No. 10/480,762 with mail date May 3, 2005.

Office Action from currently pending U.S. Appl. No. 10/480,762 with mail date Jul. 12, 2005.

Response & Amendment from currently pending U.S. Appl. No. 10/480,762 with mail date Nov. 8, 2005.

Interview Summary from currently pending U.S. Appl. No. 10/480,762 conducted May 31, 2006.

Response & Amendment from currently pending U.S. Appl. No. 10/480,762 with mail date Jul. 19, 2006.

Office Action from currently pending U.S. Appl. No. 10/480,762 with mail date Sep. 27, 2006.

Response Under 37 C.F.R. §1.111 from currently pending U.S. Appl. No. 10/480,762 with mail date Mar. 27, 2007.

Notice of Allowance & Fee(s) Due from currently pending U.S. Appl. No. 10/480,762 with mail date Jun. 28, 2007.

Comments on Statement of Reasons for Allowance from currently pending U.S. Appl. No. 10/480,762 sent by facsimile Aug. 7, 2007.

Office Action from currently pending U.S. Appl. No. 10/536,857 with mail date Mar. 1, 2006.

Response to Restriction Requirement from currently pending U.S. Appl. No. 10/536,857 with mail date Mar. 23, 2006.

Office Action from currently pending U.S. Appl. No. 10/536,857 with mail date May 9, 2006.

Amendment from currently pending U.S. Appl. No. 10/536,857 with mail date Sep. 1, 2006.

Office Action from currently pending U.S. Appl. No. 10/536,857 with mail date Nov. 15, 2006.

Amendment from currently pending U.S. Appl. No. 10/536,857 with mail date Apr. 13, 2007.

Notice of Allowance & Fee(s) Due from currently pending U.S. Appl. No. 10/536,857 with mail date Jun. 4, 2007.

* cited by examiner

PROCESS FOR PREPARING 1-BUTENE POLYMERS

This application is the U.S. national phase of International Application PCT/EP2003/012236, filed Nov. 3, 2003, claiming priority to European Patent Application 02080120.5 filed Dec. 4, 2002, and the benefit under 35 U.S.C. 119(e) of U.S. Provisional Application No. 60/431,803, filed Dec. 9, 2002; the disclosures of International Application PCT/EP2003/012236, European Patent Application 02080120.5 and U.S. Provisional Application No. 60/431,803, each as filed, are incorporated herein by reference.

The present invention relates to a process for polymerizing 1-butene by using a substituted bridged bis-indenyl metallocene compound.

1-Butene polymers are well known in the art. In view of their good properties in terms of pressure resistance, creep resistance, and impact strength, they are widely used for example in the manufacture of pipes for metal pipe replacement, easy-open packaging and films.

The 1-butene (co)polymers are generally prepared by polymerizing 1-butene in the presence of $TiCl_3$ based catalyst components together with diethylaluminum chloride (DEAC) as cocatalyst. In some cases mixtures of diethyl aluminum iodide (DEAI) and DEAC are used. The polymers obtained, however, generally do not show satisfactory mechanical properties. Furthermore, in view of the low yields obtainable with the $TiCl_3$ based catalysts, the 1-butene polymers prepared with these catalysts have a high content of catalyst residues (generally more than 300 ppm of Ti) which lowers the properties of the polymers and makes necessary to carry out a subsequent deashing step.

1-Butene (co)polymers can also be obtained by polymerizing the monomers in the presence of a stereospecific catalyst comprising: (A) a solid component comprising a Ti compound and an electron-donor compound supported on $MgCl_2$; (B) an alkylaluminum compound and, optionally, (C) an external electron-donor compound. A process of this type is disclosed in EP-A-172961 and WO99/45043.

Recently metallocene compounds have been used for producing 1-butene polymers. In Macromolecules 1995, 28, 1739–1749, rac-dimethylsilylbis(4,5,6,7-tetrahydro-1-indenyl)zirconium dichloride and methylaluminoxane have been used for polymerizing 1-butene; even if the yield of the process is not indicated, the number average molecular weight (Mn) of the obtained polymers is very low.

In Macromol. Rapid Commun. 18, 581–589 (1997) rac and meso-[dimethylsilylenebis(2,3,5-trimethyl-cyclopentadienyl)]zirconium dichloride have been used for the polymerization of 1-butene; the yields of the process and the molecular weight of the obtained polymers are rather low.

More recently, in Macromolecules 2000, 33, 1955–1956 $Me_2Si(2-Me-4,5-BzoInd)_2ZrCl_2$, $Me_2Si(2-Me-4-PhInd)_2ZrCl_2$ and $Me_2Si(Ind)_2ZrCl_2$ have been tested in the polymerization of 1-butene. The obtained polymers possesses molecular weights higher than the ones described in the previous documents, nevertheless they can be further improved; moreover the activities of these catalysts are not satisfactory, as shown in the comparative examples of the present application.

WO 99/46270 relates to a process for synthesizing bridged metallocene complexes containing a neutral diene ligand, comprising the step of contacting a metal complex of formula $MX_2D$ with a compound of formula $(L\text{---}A\text{---}L)M''_n$ wherein M is titanium, zirconium or hafnium in the +2 formal oxidation state; M" is hydrogen, a group 1 metal cation, a group 2 metal or zinc dication and the like; L is an anionic ligand bonded to A; A is a divalent bridge; X is a monovalent anionic leaving group and D is a neutral substituted derivative of 1,3-butadiene. In example 14, a complex of formula (d) was prepared

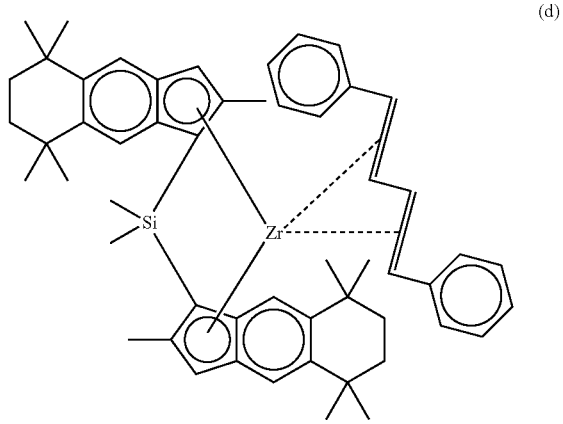

(d)

This compound is not used for polymerizing 1-butene.

Therefore it would be desirable to develop a process that allows to obtain 1-butene polymer with high molecular weight and in high yield.

An object of the present invention is a process for preparing 1-butene polymers optionally containing up to 30% by mol of units derived from at least one monomer selected from ethylene, propylene or an alpha olefin of formula $CH_2\!\!=\!\!CHZ$, wherein Z is a $C_3\text{--}C_{10}$ alkyl group, comprising polymerizing 1-butene and optionally ethylene, propylene or said alpha-olefin, in the presence of a catalyst system obtainable by contacting:

a) at least a metallocene compound of formula (I):

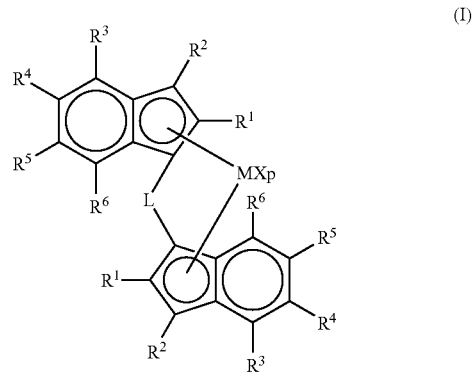

(I)

wherein:
M is a transition metal belonging to group 3, 4, 5, 6 or to the lanthanide or actinide groups in the Periodic Table of the Elements; preferably M is titanium, zirconium or hafnium;

p is an integer from 0 to 3, preferably p is 2, being equal to the formal oxidation state of the metal M minus 2;

X, equal to or different from each other, are hydrogen atoms, halogen atoms, R, OR, $OSO_2CF_3$, OCOR, SR, $NR_2$ or $PR_2$ groups, wherein R is a linear or branched, saturated or unsaturated $C_1\text{--}C_{20}$ alkyl, $C_3\text{--}C_{20}$ cycloalkyl, $C_6\text{--}C_{20}$ aryl, $C_7\text{--}C_{20}$ alkylaryl or $C_7\text{--}C_{20}$ arylalkyl radical, optionally containing heteroatoms belonging to groups 13–17 of the Periodic Table of the Elements; or two X can optionally form a substituted or unsubstituted butadienyl radical or a OR'O group wherein R' is a divalent radical selected from $C_1$–$C_{20}$ alkylidene, $C_6$–$C_{40}$ arylidene, $C_7$–$C_{40}$ alkylarylidene and $C_7$–$C_{40}$ arylalkylidene radicals; preferably X is a hydrogen atom, a halogen atom or a R group; more preferably X is chlorine or a methyl radical;

$R^1$, equal to or different from each other, are linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radicals, optionally containing one or more heteroatoms belonging to groups 13–17 of the Periodic Table of the Elements; preferably $R^1$ is a $C_1$–$C_{20}$-alkyl radical; more preferably it is a methyl or ethyl radical;

$R^2$, $R^3$ and $R^6$, equal to or different from each other, are hydrogen atoms or linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radicals, optionally containing one or more heteroatoms belonging to groups 13–17 of the Periodic Table of the Elements; preferably $R^2$, $R^3$ and $R^6$ are hydrogen atoms;

$R^4$ and $R^5$, form together a condensed saturated or unsaturaded $C_3$–$C_7$-membered ring preferably a $C_4$–$C_6$-membered ring, optionally containing heteroatoms belonging to groups 13–16 of the Periodic Table of the Elements; every atom forming said ring being substituted with $R^7$ radicals; that means that the valence of each atom forming said ring is filled with $R^7$ groups, wherein $R^7$, equal to or different from each other, are hydrogen or linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radicals, optionally containing one or more heteroatoms belonging to groups 13–17 of the Periodic Table of the Elements; preferably $R^7$ is a hydrogen atom or a linear or branched, saturated or unsaturated $C_1$–$C_{20}$-alkyl radical; more preferably it is a hydrogen atom or a methyl or ethyl radical;

L is a divalent bridging group selected from $C_1$-$C_{20}$ alkylidene, $C_3$-$C_{20}$ cycloalkylidene, $C_6$-$C_{20}$ arylidene, $C_7$-$C_{20}$ alkylarylidene, or a $C_7$-$C_{20}$ arylalkylidene radicals, optionally containing heteroatoms belonging to groups 13–17 of the Periodic Table of the Elements, or it is a silylidene radical containing up to 5 silicon atoms; preferably L is $Si(R^8)_2$ wherein $R^8$ is a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radical; more preferably L is $Si(CH_3)_2$ or $SiPh_2$;

b) at least an alumoxane or a compound able to form an alkylmetallocene cation; and c) optionally an organo aluminum compound.

Preferably the compound of formula (I) is in the racemic (rac) form.

Preferably the compound of formula (I) has formula (IIa) or (IIb)

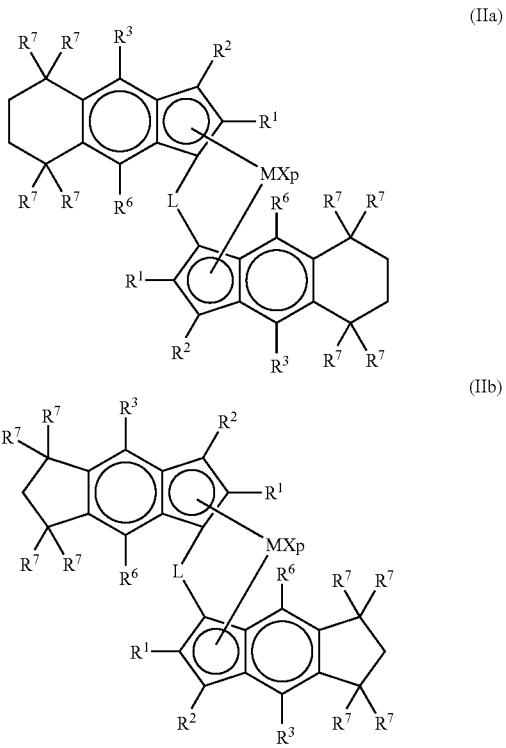

wherein:

M, X, p, L, $R^1$, $R^2$, $R^3$, $R^6$ and $R^7$ have the meaning described above.

Compounds of formula (I) can be prepared with a process comprising the following steps:

a) contacting a ligand of formula (III)

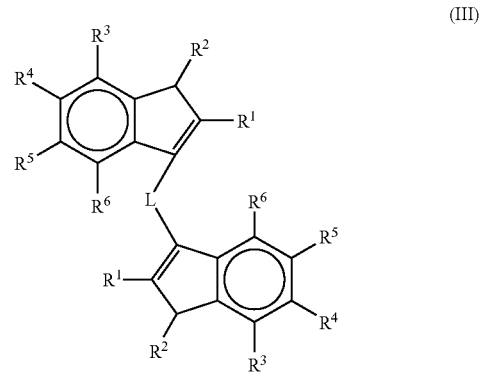

and/or its double bond isomers wherein $R^1$, $R^2$, $R^3$, $R^4$, $R^5$, $R^6$, and L have the meaning described above with a base selected from $T_jB$, $TMgT^1$, sodium and potassium hydride, metallic sodium and potassium, wherein B is an alkaline or alkali-earth metal; and j is 1 or 2, j being equal to 1 when B is an alkaline metal, preferably lithium, and j being equal to 2 when B is an alkali-earth metal; T is a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl group, optionally containing one or more Si or Ge atoms; preferably T is methyl or butyl radical; $T^1$ is an halogen atom or a group OR" wherein R" is a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radical, optionally containing one or more heteroatoms belonging to groups 13–17 of the Periodic Table of the Elements; preferably $T^1$ is an halogen atom, more preferably bromine; wherein the molar ratio between said base and the ligand of the formula (III) and is at least 2:1; excess of said base can be used; and b) contacting the product obtained in step a) with a compound of formula $MX_4$ wherein M and X have the meaning described above.

The process is preferably carried out in an aprotic solvent, either polar or apolar. Said aprotic solvent is preferably an aromatic or aliphatic hydrocarbon, optionally halogenated, or an ether; more preferably it is selected from benzene, toluene, pentane, hexane, heptane, cyclohexane, dichloromethane, diethylether, tetrahydrofurane and mixtures thereof. The above process is carried out at a temperature ranging from −100° C. to +80° C., more preferably from −20° C. to +70° C.

The ligands of formula (III) can be obtained with a process comprising the following steps:

a) contacting a compound of formula (IVa):

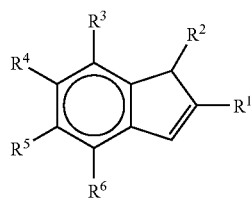

(IVa)

and/or its double bond isomer wherein $R^1$, $R^2$, $R^3$, $R^4$, $R^5$ and $R^6$ are defined as above; with a base selected from $T_jB$, $TMgT^1$, sodium and potassium hydride, metallic sodium and potassium; wherein T, j, B and $T^1$ are defined as above, and wherein the molar ratio between said base and the compound of the formula (IVa) is at least 1:1; excess of said base can be used;

b) contacting the anionic compound obtained in step a) with a compound of formula (IVb):

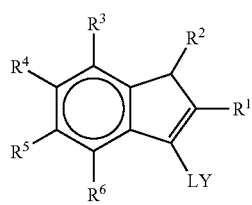

(IVb)

wherein $R^1$, $R^2$, $R^3$, $R^4$, $R^5$, $R^6$ and L are defined as above and Y is chlorine, bromine and iodine, preferably Y is chlorine or bromine.

When the indenyl moieties are the same, i.e. the substituents $R^1$, $R^2$, $R^3$, $R^4$, $R^5$ and $R^6$ are the same on both the indenyl moieties, an alternative process for preparing the ligand of formula (III) comprises the following steps:

a) contacting a compound of formula (IVa):

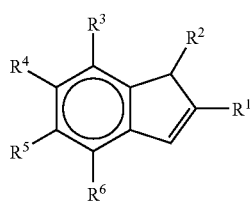

(IVa)

and/or its double bond isomer wherein $R^1$, $R^2$, $R^3$, $R^4$, $R^5$ and $R^6$ are defined as above; with a base selected from $T_jB$, $TMgT^1$, sodium and potassium hydride, metallic sodium and potassium; wherein T, j, B, and $T^1$ are defined as above, and wherein the molar ratio between said base and the compound of the formula (IVa) is at least 1:1, excess of said base can be used;

b) reacting the product obtained in step a) with a compound of formula YLY, wherein L and Y are defined as above, wherein the molar ratio between the compound obtained in step a) and the compound of formula YLY is at least 2:1; excess of the compound obtained instep a) can be used.

Alumoxanes used as component b) can be obtained by reacting water with an organo-aluminium compound of formula $H_jAlU_{3-j}$ or $H_jAl_2U_{6-j}$, where the U substituents, same or different, are hydrogen atoms, halogen atoms, $C_1$–$C_{20}$-alkyl, $C_3$–$C_{20}$-cyclalkyl, $C_6$–$C_{20}$-aryl, $C_7$–$C_{20}$-alkylaryl or $C_7$–$C_{20}$-arylalkyl radicals, optionally containing silicon or germanium atoms, with the proviso that at least one U is different from halogen, and j ranges from 0 to 1, being also a non-integer number. In this reaction the molar ratio of Al/water is preferably comprised between 1:1 and 100:1.

The molar ratio between aluminium and the metal of the metallocene is generally comprised between about 10:1 and about 30000:1, preferably between about 100:1 and about 5000:1.

The alumoxanes used in the catalyst according to the invention are considered to be linear, branched or cyclic compounds containing at least one group of the type:

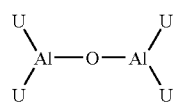

wherein the substituents U, same or different, are defined above.

In particular, alumoxanes of the formula:

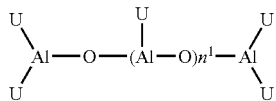

can be used in the case of linear compounds, wherein $n^1$ is 0 or an integer of from 1 to 40 and the substituents U are defined as above; or alumoxanes of the formula:

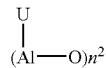

can be used in the case of cyclic compounds, wherein $n^2$ is an integer from 2 to 40 and the U substituents are defined as above.

Examples of alumoxanes suitable for use according to the present invention are methylalumoxane (MAO), tetra-(isobutyl)alumoxane (TIBAO), tetra-(2,4,4-trimethyl-pentyl)alumoxane (TIOAO), tetra-(2,3-dimethylbutyl)alumoxane (TDMBAO) and tetra-(2,3,3-trimethylbutyl)alumoxane (TTMBAO).

Particularly interesting cocatalysts are those described in WO 99/21899 and in WO01/21674 in which the alkyl and aryl groups have specific branched patterns.

Non-limiting examples of aluminium compounds that can be reacted with water to give suitable alumoxanes (b), described in WO 99/21899 and WO01/21674, are: tris(2,3,3-trimethyl-butyl)aluminium, tris(2,3-dimethyl-hexyl)aluminium, tris(2,3-dimethyl-butyl)aluminium, tris(2,3-dimethyl-pentyl)aluminium, tris(2,3-dimethyl-heptyl)aluminium, tris(2-methyl-3-ethyl-pentyl)aluminium, tris(2-methyl-3-ethyl-hexyl)aluminium, tris(2-methyl-3-ethyl-heptyl)aluminium, tris(2-methyl-3-propyl-hexyl)aluminium, tris(2-ethyl-3-methyl-butyl)aluminium, tris(2-ethyl-3-methyl-pentyl)aluminium, tris(2,3-diethyl-pentyl)aluminium, tris(2-propyl-3-methyl-butyl)aluminium, tris(2-isopropyl-3-methyl-butyl)aluminium, tris(2-isobutyl-3-methyl-pentyl)aluminium, tris(2,3,3-trimethyl-pentyl)aluminium, tris(2,3,3-trimethyl-hexyl)aluminium, tris(2-ethyl-3,3-dimethyl-butyl)aluminium, tris(2-ethyl-3,3-dimethyl-pentyl)aluminium, tris(2-isopropyl-3,3-dimethyl-butyl)aluminium, tris(2-trimethylsilyl-propyl)aluminium, tris(2-methyl-3-phenyl-butyl)aluminium, tris(2-ethyl-3-phenyl-butyl)aluminium, tris(2,3-dimethyl-3-phenyl-butyl)aluminium, tris(2-phenyl-propyl)aluminium, tris[2-(4-fluoro-phenyl)-propyl]aluminium, tris[2-(4-chloro-phenyl)-propyl]aluminium, tris[2-(3-isopropyl-phenyl)-propyl]aluminium, tris(2-phenyl-butyl)aluminium, tris(3-methyl-2-phenyl-butyl)aluminium, tris(2-phenyl-pentyl)aluminium, tris[2-(pentafluorophenyl)-propyl]aluminium, tris[2,2-diphenyl-ethyl]aluminium and tris[2-phenyl-2-methyl-propyl]aluminium, as well as the corresponding compounds wherein one of the hydrocarbyl groups is replaced with a hydrogen atom, and those wherein one or two of the hydrocarbyl groups are replaced with an isobutyl group.

Amongst the above aluminium compounds, trimethylaluminium (TMA), triisobutylaluminium (TIBA), tris(2,4,4-trimethyl-pentyl)aluminium (TIOA), tris(2,3-dimethylbutyl)aluminium (TDMBA) and tris(2,3,3-trimethylbutyl)aluminium (TTMBA) are preferred.

Non-limiting examples of compounds able to form an alkylmetallocene cation are compounds of formula $D^+E^-$, wherein $D^+$ is a Brønsted acid, able to donate a proton and to react irreversibly with a substituent X of the metallocene of formula (I) and $E^-$ is a compatible anion, which is able to stabilize the active catalytic species originating from the reaction of the two compounds, and which is sufficiently labile to be removed by an olefinic monomer. Preferably, the anion $E^-$ comprises one or more boron atoms. More preferably, the anion $E^-$ is an anion of the formula $BAr_4^{(-)}$, wherein the substituents Ar which can be identical or different are aryl radicals such as phenyl, pentafluorophenyl or bis(trifluoromethyl)phenyl. Tetralis-pentafluorophenyl borate is particularly preferred compound, as described in WO 91/02012. Moreover, compounds of formula $BAr_3$ can be conveniently used. Compounds of this type are described, for example, in the International patent application WO 92/00333. Other examples of compounds able to form an alkylmetallocene cation are compounds of formula $BAr_3P$ wherein P is a substituted or unsubstituted pyrrol radical. These compounds are described in WO01/62764. Compounds containing boron atoms can be conveniently supported according to the description of DE-A-19962814 and DE-A-19962910. All these compounds containing boron atoms can be used in a molar ratio between boron and the metal of the metallocene comprised between about 1:1 and about 10:1; preferably 1:1 and 2.1; more preferably about 1:1.

Non limiting examples of compounds of formula $D^+E^-$ are:
Triethylammoniumtetra(phenyl)borate,
Tributylammoniumtetra(phenyl)borate,
Trimethylammoniumtetra(tolyl)borate,
Tributylammoniumtetra(tolyl)borate,
Tributylammoniumtetra(pentafluorophenyl)borate,
Tributylammoniumtetra(pentafluorophenyl)aluminate,
Tripropylammoniumtetra(dimethylphenyl)borate,
Tributylammoniumtetra(trifluoromethylphenyl)borate,
Tributylammoniumtetra(4-fluorophenyl)borate,
N,N-Dimethylbenzylammonium-tetrakispentafluorophenylborate,
N,N-Dimethylhexylamonium-tetrakispentafluorophenylborate,
N,N-Dimethylaniliniumtetra(phenyl)borate,
N,N-Diethylaniliniumtetra(phenyl)borate,
N,N-Dimethylaniliniumtetrakis(pentafluorophenyl)borate,
N,N-Dimethylaniliniumtetrakis(pentafluorophenyl)aluminate,
N,N-Dimethylbenzylammonium-tetrakispentafluorophenylborate,
N,N-Dimethylhexylamonium-tetrakispentafluorophenylborate,
Di(propyl)ammoniumtetrakis(pentafluorophenyl)borate,
Di(cyclohexyl)ammoniumtetrakis(pentafluorophenyl)borate,
Triphenylphosphoniumtetrakis(phenyl)borate,
Triethylphosphoniumtetrakis(phenyl)borate,
Diphenylphosphoniumtetrakis(phenyl)borate,
Tri(methylphenyl)phosphoniumtetrakis(phenyl)borate,
Tri(dimethylphenyl)phosphoniumtetrakis(phenyl)borate,
Triphenylcarbeniumtetrakis(pentafluorophenyl)borate,
Triphenylcarbeniumtetrakis(pentafluorophenyl)aluminate,
Triphenylcarbeniumtetrakis(phenyl)aluminate,
Ferroceniumtetrakis(pentafluorophenyl)borate,
Ferroceniumtetrakis(pentafluorophenyl)aluminate.
Triphenylcarbeniumtetrakis(pentafluorophenyl)borate, and N,N-Dimethylaniliniumtetrakis(pentafluorophenyl)borate.

Organic aluminum compounds used as compound c) are those of formula $H_jAlU_{3-j}$ or $H_jAl_2U_{6-j}$ as described above.

The polymerization process of the present invention can be carried out in liquid phase. The polymerization medium can be 1-butene optionally in the presence of an inert hydrocarbon solvent. Said hydrocarbon solvent can be either aromatic (such as toluene) or aliphatic (such as propane, hexane, heptane, isobutane, cyclohexane and 2,2,4-trimethylpentane). Otherwise the polymerization process of the present invention can be carried out in a gas phase. Preferably the polymerization is carried out by using liquid 1-butene i.e. the monomer, as the polymerization medium (bulk polymerization).

The catalyst system of the present invention can also be supported on an inert carrier. This is achieved by depositing the metallocene compound a) or the product of the reaction thereof with the component b), or the component b) and then the metallocene compound a) on an inert support such as, for example, silica, alumina, Al—Si, Al—Mg mixed oxides, magnesium halides, styrene/divinylbenzene copolymers, polyethylene or polypropylene. The supportation process is carried out in an inert solvent, such as hydrocarbon selected from toluene, hexane, pentane and propane and at a temperature ranging from 0° C. to 100° C., more from 30° C. to 60° C.

A particularly suitable process for supporting the catalyst system is described in WO01/44319, wherein the process comprises the steps of:
(a) preparing a catalyst solution comprising a soluble catalyst component;
(b) introducing into a contacting vessel:
  (i) a porous support material in particle form, and
  (ii) a volume of the catalyst solution not greater than the total pore volume of the porous support material introduced;
(c) discharging the material resulting from step (b) from the contacting vessel and suspending it in an inert gas flow, under such conditions that the solvent evaporates; and
(d) reintroducing at least part of the material resulting from step (c) into the contacting vessel together with another volume of the catalyst solution not greater than the total pore volume of the reintroduced material.

A suitable class of supports comprises porous organic supports functionalized with groups having active hydrogen atoms. Particularly suitable are those in which the organic support is a partially crosslinked styrene polymer. Supports of this type are described in EP 633 272.

Another class of inert supports particularly suitable for use according to the invention is that of polyolefin porous prepolymers, particularly polyethylene.

A further suitable class of inert supports for use according to the invention is that of porous magnesium halides, such as those described in WO 95/32995.

The polymerization temperature preferably ranges from 0° C. to 250° C.; preferably comprised between 20° C. and 150° C. and, more particularly between 40° C. and 90° C.

Generally, the polymers of the present invention are endowed with a narrow molecular weight distribution $M_w/M_n$, when the metallocene used is a pure isomer, $M_w/M_n$ is preferably lower than 3, more preferably lower than 2.5.

The molecular weight distribution can be varied by using mixtures of different metallocene compounds or mixtures of the metallocene compound of formula (I) and a Ziegler-Natta catalyst or by carrying out the polymerization in several stages at different polymerization temperatures and/or different concentrations of the molecular weight regulators and/or different monomer concentration.

The polymerization yield depends on the purity of the transition metal organometallic catalyst compound (the metallocene compound of formula (I)) a) in the catalyst, therefore, said compound can be used as such or can be subjected to purification treatments before use. With the process of the present invention 1-butene can be homopolymerized with high yields and the isotactic polymers obtained show a high molecular weight and a relatively low melting point. The obtained polymer is endowed with improved flexibility and elongation at break.

When 1-butene is copolymerized with ethylene, propylene or an alpha olefin of formula $CH_2\!=\!CHZ$ wherein Z is a $C_3$–$C_{10}$ alkyl group a copolymer having a comonomer derived unit content up to 30% by mol can be obtained.

Preferably the comonomer content ranges from 0.5 to 20% by mol. Preferred comonomers are ethylene, propylene or 1-hexene.

A further object of the present invention is a metallocene compound of formula (IIb):

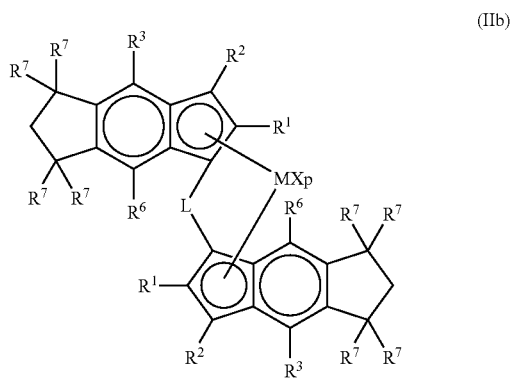

(IIb)

wherein M, p, L, $R^1$, $R^2$, $R^3$, $R^6$, $R^7$ and X have the meaning described above.

The metallocene compounds of formula (IIb) can be prepared according to the process described above starting from the ligand of formula (V) or its corresponding double bond isomers:

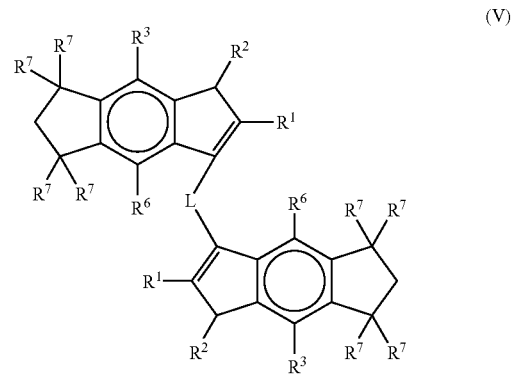

(V)

wherein L, $R^1$, $R^2$, $R^3$, $R^6$, and $R^7$ are described above; preferably $R^1$ is a $C_1$–$C_{20}$-alkyl radical; more preferably it is a methyl or ethyl radical; $R^2$, $R^3$ and $R^6$ are preferably hydrogen atoms; preferably $R^7$ is a linear or branched, saturated or unsaturated $C_1$–$C_{20}$-alkyl radical; more preferably it is a methyl or ethyl radical; preferably L is $Si(R^8)_2$ wherein $R^8$ is a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radical; more preferably L is $Si(CH_3)_2$ or $SiPh_2$. Instead of using the ligand of formula (III)

Thus it is a further object of the present invention a process for preparing the metallocene compounds of formula (IIb) comprising the following steps:
a) contacting a ligand of formula (V)

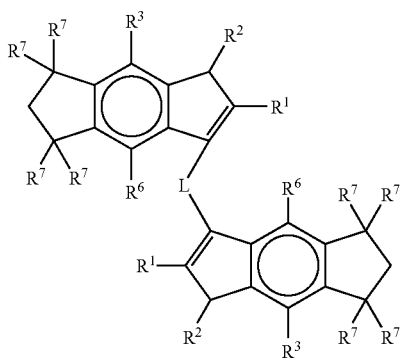

(V)

and/or its double bond isomer
wherein: $R^1, R^2, R^3, R^5, R^6, R^7$ and L are described above
with a base of formula $T_jB$ or $TMgT^1$, or sodium or potassium hydride, or metallic sodium or potassium; wherein B is an alkaline or alkali-earth metal; and j is 1 or 2, j being equal to 1 when B is an alkaline metal, and j being equal to 2 when B is an alkali-earth metal; T is selected from the group consisting of linear or branched, saturated or unsaturated $C_1-C_{20}$ alkyl, $C_3-C_{20}$ cycloalkyl, $C_6-C_{20}$ aryl, $C_7-C_{20}$ alklaryl or $C_7-C_{20}$ arylalkyl groups, optionally containing one or more Si or Ge atoms; $T^1$ is an halogen atom or a group OR" wherein R" is a linear or branched, saturated or unsaturated $C_1-C_{20}$-alkyl, $C_3-C_{20}$-cycloalkyl, $C_6-C_{20}$-aryl, $C_7-C_{20}$-alkylaryl or $C_7-C_{20}$-arylalkyl radicals, optionally containing one or more heteroatoms belonging to groups 13–17 of the Periodic Table of the Elements; wherein the molar ratio between said base and the ligand of the formula (V) is at least 2:1; excess of said base can be used; and b) contacting the product obtained in step a) with a compound of formula $MX_4$ wherein M and X have been described above.

The compound of formula (V) can be prepared starting from the compounds of formula (VI) and (VII)

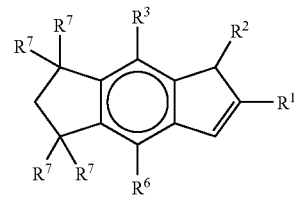

(VI)

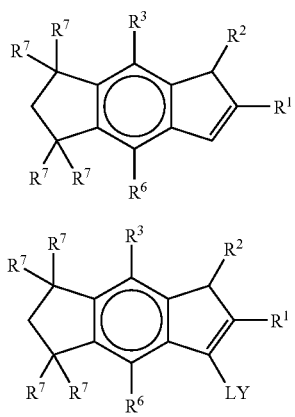

(VII)

according to the processes described above by using the compounds of formulas (VI) and (VII) instead of the compound of formulas (IVa) and (IVb).

Thus it is a further object of the present invention is a process for preparing the ligand of formula (V) comprising the following steps:
a) contacting a compound of formula (VI):

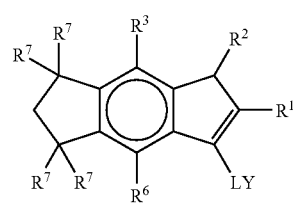

(VI)

or its double bonds isomer
wherein: $R^1, R^2, R^3, R_6$, and $R^7$ are described above;
with a base of formula $T_jB$ or $TMgT^1$, or sodium or potassium hydride, or metallic sodium or potassium; wherein T, j, B, and $T^1$ are described above, wherein the molar ratio of said base and the compound of the formula (VI) is at least 1:1; excess of said base can be used;

b) contacting the anionic compounds obtained in step a) with a compound of formula (VII):

(VII)

or its double bonds isomer
wherein $R^1, R^2, R^3, R^6, R^7$ and L are described above and Y is a halogen radical selected from the group consisting of chloride, bromide and iodide.

When the substituents $R^1, R^2, R^3, R^4, R^5$ and $R^6$ are the same in both the indenyl moieties an alternative process for preparing the ligand of formula (V) comprises the following steps:
a) contacting a compound of formula (VI):

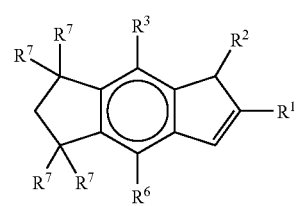

(VI)

or its double bonds isomer
wherein: $R^1, R^2, R^3, R^6, R^7$ and L are described above; with a base of formula $T_jB$ or $TMgT^1$, or sodium or potassium hydride, or metallic sodium or potassium; wherein T, j, B, and $T^1$ are described above, wherein the molar ratio between said base and the compound of the formula (VI) is at least 1:1; excess of said base can be used; and b) reacting the product obtained in step a) with a compound of formula YLY, wherein L and Y are described above wherein the molar ratio between the compound obtained in step a) and the compound of formula YLY is at least 2:1; excess of compound obtained in step a) can be used.

The following examples are given for illustrative purpose and do not intend to limit the invention.

EXAMPLES

General Procedures

All operations were performed under nitrogen by using conventional Shlenk-line techniques. Solvents were purified by degassing with nitrogen and passing over activated $Al_2O_3$ and stored under nitrogen. All compounds were analyzed by $^1$H-NMR and $^{13}$C-NMR on a DPX 200 Bruker spectrometer ($CDCl_3$, referenced against the peak of residual $CHCl_3$ at 7.25 ppm). Due to the low solubility of the Zirconocene, the $^{13}$C-NMR spectra of this compound were performed on a Bruker DPX 400 in $CD_2Cl_4$ at 120° C.

Example 1

Synthesis of $Me_2Si[2-Me-5,6(tetramethylcyclotrymethylen)indenyl]_2ZrCl_2[A1]$

Synthesis of 1,1,3,3-Tetramethylindane

A mixture of 117.26 g of α-Methylstyrene (Aldrich 99%, 0.98 mol) and 73.0 g of t-Butanol (Aldrich 99%, 0.97 mol) were slowly added (1 hour) to a mixture of 200 g of acetic acid and 200 g of sulfuric acid, previously warmed at 40° C. The suspension so-obtained was stirred 30 min at 40° C. and then the 2 layers were separated. The organic layer was washed with a 0.7 M NaOH acqueous solution (3×50 ml, neutrality) and water (2×50 ml). The opaque yellow solution obtained was then distilled at 26 mbar. At about 100° C. a colourless transparent liquid was distilled off (28.43 g), which was characterized by NMR as pure 1,1,3,3 tetramethylindane (16.6% yield).

$^1$H-NMR ($CDCl_3$, δ, ppm): 1.39 (s, $CH_3$, H8 and H9, 12H); 1.99 (s, $CH_2$, H2, 2H); 7.17–7.30 (m, Ar, H4, H5, H6 and H7, 4H). $^{13}$C-NMR ($CDCl_3$, δ, ppm): 31.56 ($CH_3$, C8 and C9, 4C); 42.51 (C, C1 and C3, 2C); 56.60 ($CH_2$, C2, 1C); 122.45 and 126.69 (Ar, C4, C5, C6 and C7, 4C); 151.15 (Ar, C3a and C7a, 2C).

Synthesis of 2,5,5,7,7-Pentamethyl-2,3,5,6,7-pentahydro-s-indacen-1-one 50.71 g of $AlCl_3$ (Aldrich 99%, 376.5 mmol) were slowly added (30 min) to a mixture of 28.43 g of 1,1,3,3 tetramethylindane (163.1 mmol), 38.32 g of 2-Bromoisobutyryl bromide (Aldrich 98%, 163.3 mmmol) and 500 ml of $CH_2Cl_2$ at 0° C. The solution colour turned yellow and finally dark red. The suspension was stirred 17 hours at room temperature and then quenched with 200 g of ice. The green organic layer was washed with a 1 M HCl acqueous solution (1×200 ml), a saturated $NaHCO_3$ solution (2×200 ml) and water (2×200 ml). Then it was dried over $Na_2SO_4$, filtered and evaporated to dryness under reduced pressure to give 38.23 g (96.7% yield) of a green solid. This solid was determined by GC-MS to contain 76.7% of the desired product. This was treated with 50 ml of MeOH and filtered. The white residue was washed with MeOH and dried to obtain 20.28 g of a white powder. The filtrate was stored at −20° C., to obtain 3.95 g of a white powder, collected with the previous one. This powder was characterized by NMR as pure 2,5,5,7,7-Pentamethyl-2,3,5, 6,7-pentahydro-s-indacen-1-one. The yield on the isolated pure product was 61.3%.

$^1$H-NMR ($CDCl_3$, δ, ppm): 1.27 (s, $CH_3$, H9, 3H); 1.31 (s, $CH_3$, H11, 6H); 1.33 (s, $CH_3$, H10, 6H); 1.95 (s, $CH_2$, H6, 2H),; 2.62-2.79 (m, $CH_2$ and CH, H2 and H3, 2H); 3.28–3.37 (m, $CH_2$, H3, 1H); 7.15 (s, Ar, H4, 1H); 7.51 (s, Ar, H8, 1H). $^{13}$C-NMR ($CDCl_3$, δ, ppm): 16.34 ($CH_3$, C9, 1C); 31.28, 31.30 ($CH_3$, C10, 2C); 31.50, 31.55 ($CH_3$, C11, 2C); 34.73 ($CH_2$, C3, 1C); 41.86 (C, C7, 1C); 42.38 (CH, C2, 1C); 42.52 (C, C5, 1C); 56.44 ($CH_2$, C6, 1C); 117.87 (Ar, C8, 1C); 120.22 (Ar, C4, 1C); 135.67 (Ar, C8a, 1C); 151.69 (Ar, C7a, 1C); 152.91 (Ar, $C_3$a, 1C); 159.99 (Ar, C4a, 1C); 208.96 (C=O, C1, 1C).

Synthesis of 2,5,5,7,7-Pentamethyl-1,2,3,5,6,7-hexahydro-s-indacen-1-ol

A suspension of 2.70 g of pure 2,5,5,7,7-Pentamethyl-2,3, 5,6,7-pentahydro-s-indacen-1-one (11.1 mmol) in 15 ml of Ethanol was treated with 0.46 g of $NaBH_4$ (Aldrich 98%, 11.9 mmol) at room temperature. An opaque yellowish solution was obtained. After 18 hours stirring at room temperature, the solution was treated with 2 ml of acetone and then evaporated to dryness under reduced pressure. The yellowish gel obtained was treated with 35 ml of toluene and 35 ml of water. The two layers were separated. The acqueous layer was washed with 20 ml of toluene. The organic layer was washed with a 10% $NH_4Cl$ acqueous solution (2×20 ml), dried over $Na_2SO_4$ and filtered. The filtrate was evaporated to dryness under reduced pressure to give 2.54 g of a white powder (93.7% yield), which was characterized by NMR as pure 2,5,5,7,7-Pentamethyl-1,2,3,5,6,7-hexahydro-s-indacen-1-ol. Owing to the presence of 2 chiral centers (carbons C1 and C2), this sample is characterized by the presence of 2 isomers: indicated with A and B. The A:B ratio observed by $^1$H-NMR spectrum was 60:40.

$^1$H-NMR ($CDCl_3$, δ, ppm): 1.17 (d, $CH_3$, H9, 3H, J=6.85, isomer B); 1.27 (d, $CH_3$, H9, 3H, J=6.85, isomer A); 1.31 (s, $CH_3$, H10 and H11, 12H, isomer A and B); 1.48 (d, OH, 1H, J=6.85, isomer A); 1.80 (d, OH, 1H, J=6.85, isomer B); 1.93 (s, $CH_2$, H6, 2H, isomer A and B); 2.17–3.13 (m, CH and $CH_2$, H2 and H3, 3H, isomer A and B); 4.69 (t, CH, H1, 1H, J=7.24, isomer A); 4.95 (t, CH, H1, 1H, J=8.57, isomer B); 6.95 (s, Ar, H4, 1H, isomer A); 6.97 (s, Ar, H4, 1H, isomer B); 7.14 (s, Ar, H8, 1H, isomer A); 7.17 (s, Ar, H8, 1H, isomer B). $^{13}$C-NMR ($CDCl_3$, δ, ppm): 13.88 ($CH_3$, C9, 1C, isomer B); 17.87 ($CH_3$, C9, 1C, isomer A); 31.58, 31.65, 31.69, 31.75 ($CH_3$, C10 and C11, 4C, isomer A and B); 37.64–37.75 ($CH_2$, C3, 1C); 39.62 (CH, C2, 1C, isomer B); 42.11–42.16 (C, C5 and C7, 2C, isomer A and B); 45.99 (CH, C2, 1C, isomer A); 56.89 ($CH_2$, C6, 1C); 77.51 (C—OH, C1, 1C, isomer B); 82.78 (C—OH, C1, 1C, isomer A); 117.80, 118.62, 118.80 (Ar, C4 and C8, 2C, isomer A and B); 140.68–152.10 (Ar, $C_3$a, C4a, C7a, C8a).

Synthesis of 1,1,3,3,6-Pentamethyl-1,2,3,5-tetrahydro-s-indacene

A suspension of 24.36 g of pure 2,5,5,7,7-Pentamethyl-2, 3,5,6,7-pentahydro-s-indacen-1-one (100.5 mmol) in 100 ml of Ethanol was treated with 4.06 g of $NaBH_4$ (Aldrich 98%, 105.2 mmol) at room temperature. An opaque yellowish solution was obtained. After 4 hours stirring at room temperature, the solution was treated with 5 ml of acetone and then evaporated to dryness under reduced pressure. The yellowish gel obtained was treated with 100 ml of toluene and 40 ml of water. The two layers were separated. The acqueous layer was washed with 50 ml of toluene. The organic layer was washed with a 10% $NH_4Cl$ acqueous solution (2×30 ml), dried over $Na_2SO_4$ and filtered. The yellow filtrate was treated with 1.89 g of p-Toluenesulfonic acid monohydrate (Aldrich 98.5%, 9.8 mmol) and heated to 80° C. Formation of water with the separation of 2 layers was observed. After 5 hours stirring at 80° C. and 2 days at room temperature, the reaction was not finished (11% of alcohol), so the water formed was separated from the reaction mixture and 0.20 g of p-Toluenesulfonic acid monohydrate (Aldrich 98.5%, 1,0 mmol) were added. After 1 hour stirring at 80° C. and 16 hours at room temperature, the reaction was complete and so the mixture was treated with 50 ml of a saturated $NaHCO_3$ acqueous solution. The organic layer was separated, washed with a saturated $NaHCO_3$ acqueous solution (1×50 ml) and water (3×50 ml), dried over $Na_2SO_4$ and filtered. The yellow filtrate was evaporated to dryness under reduced pressure to give 20.89 g of a yellow liquid (91.8% yield), that crystallized after few minutes. This was characterized by NMR as pure 1,1,3,3,6-Pentamethyl-1,2,3,5-tetrahydro-s-indacene.

$^1$H-NMR ($CDCl_3$, δ, ppm): 1.38 (s, $CH_3$, H9 e H10, 12H); 2.00 (s, $CH_2$, H2, 2H); 2.18 (bs, $CH_3$, H11, 3H); 3.30 (s, $CH_2$, H5, 2H); 6.51 (s, CH, H7, 1H); 7.06 (s, Ar, H8, 1H); 7.18 (s, Ar, H4, 1H). $^{13}$C-NMR ($CDCl_3$, δ, ppm): 16.81 ($CH_3$, C11, 1C); 31.77 ($CH_3$, C9 e C10, 4C); 42.08, 42.16 (C, C1 e C3, 2C); 42.28 ($CH_2$, C5, 1C); 57.04 ($CH_2$, C2, 1C); 113.61 (Ar, C8, 1C); 117.55 (Ar, C4, 1C); 127.13 (CH, C7, 1C); 142.28 (Ar, C4a, 1C); 145.00, 145.26 (Ar and C=, C7a and C6, 2C); 146.88 (Ar, $C_3$a, 1C); 149.47 (Ar, C8a, 1C).

dimethyl-bis-(2,5,5,7,7-pentamethyl-1,5,6,7-tetrahydro-s-indacen-1-yl)-silane 8.8 ml of a 2.5 M BuLi diethyl ether solution (Aldrich, 22.0 mmol) were slowly added to a solution of 4.99 g of 1,1,3,3,6-Pentamethyl-1,2,3,5-tetrahydro-s-indacene (22.0 mmol) in 65 ml of diethyl ether at 0° C. The yellow suspension formed was then stirred at room temperature. $^1$H-NMR showed the complete formation of the lithium salt after 1 hour. So a solution of 1.51 g of Dimethyldichloro silane (Fluka 99%, 11.6 mmol) in 30 ml of THF was added to the reaction mixture at 0° C. The clear yellow suspension was then stirred at room temperature for 20 hours. Then the suspension was evaporated to dryness under reduced pressure, to give a yellow sticky solid. This was treated with 70 ml of toluene and filtered. The white residue on the frit was washed twice with 20 ml of toluene. The yellow filtrate was evaporated to dryness under reduced pressure, to give 5.67 g of a yellow sticky solid, containing the desired product (rac:meso=20:80), some starting indene (11% respect to the product) and some other unkown products. This solid was treated with 20 ml of pentane to form a pale yellow solution with a white precipitate, which was filtered and dried. 0.53 g of a white powder were obtained, which was characterized by NMR as pure rac-dimethyl-bis-(2,5,5,7,7-pentamethyl-1,5,6,7-tetrahydro-s-indacen-1-yl)-silane. The filtrate was concentrated to 10 ml and cooled at −20° C. After 20 hours a white solid (2.27 g g) was separated from the solution, which was characterized by NMR as pure dimethyl-bis-(2,5,5,7,7-pentamethyl-1,5,6,7-tetrahydro-s-indacen-1-yl)-silane (rac:meso=10:90). Other 1.12 g of pure product were then crystallized. Total yield on the pure isolated product was 57.0%.

Rac isomer $^1$H-NMR ($CDCl_3$, δ, ppm): −0.23 (s, Si—$CH_3$, 6H); 1.32 (s, $CH_3$, H11, 12H); 1.37, 1.38 (s, $CH_3$, H10, 12H); 1.97 (s, $CH_2$, H6, 4H); 2.19 (bs, $CH_3$, H9, 6H); 3.62 (s, CH, H1, 2H); 6.58 (s, CH, H3, 2H); 7.10 (s, Ar, H4, 2H); 7.27 (s, Ar, H8, 2H). $^{13}$C-NMR ($CDCl_3$, δ, ppm): −5.52 (Si—$CH_3$, 2C); 17.90 ($CH_3$, C9, 2C); 31.68, 31.80, 31.98 ($CH_3$, C10 e C11, 8C); 42.06, 42.13 (C, C5 e C7, 4C); 46.69 (CH, C1, 2C); 57.13 ($CH_2$, C6, 2C); 113.60 (Ar, C4, 2C); 117.15 (Ar, C8, 2C); 126.69 (CH, C3, 2C); 143.78 (Ar, C8a, 2C); 144.40 (Ar, C3a, 2C); 146.19 (C=, C2, 2C); 146.35 (Ar, C7a, 2C); 148.63 (Ar, C4a, 2C).

Meso isomer $^1$H-NMR ($CDCl_3$, δ, ppm): −0.29, −0.16 (s, Si—$CH_3$, 6H); 1.28, 1.30 (s, $CH_3$, H11, 12H); 1.32, 1.33 (s, $CH_3$, H10, 12H); 1.93 (s, $CH_2$, H6, 4H); 2.16 (bs, $CH_3$, H9, 6H); 3.51 (s, CH, H1, 2H); 6.57 (s, CH, H3, 2H); 7.06 (s, Ar, H4, 2H); 7.08 (s, Ar, H8, 2H). $^{13}$C-NMR ($CDCl_3$, δ, ppm): −5.04, −4.67 (Si—$CH_3$, 2C); 17.83 ($CH_3$, C9, 2C); 31.70, 31.79, 31.96 ($CH_3$, C10 e C11, 8C); 42.05, 42.12 (C, C5 e C7, 4C); 46.55 (CH, C1, 2C); 57.10 ($CH_2$, C6, 2C); 113.59 (Ar, C4, 2C); 117.29 (Ar, C8, 2C); 126.59 (CH, $C_{3,2}$C); 143.88 (Ar, C8a, 2C); 144.27 (Ar, C3a, 2C); 146.33 (C=, C2, 2C); 146.53 (Ar, C7a, 2C); 148.62 (Ar, C4a, 2C).

Synthesis of $Me_2Si$[2-Me-5,6(tetramethylcyclotrimethylen)indenyl]$_2$$ZrCl_2$|A1|

1.39 ml of a 1.5 M MeLi diethyl ether solution (Aldrich, 2.1 mmol) were slowly added to a suspension of 0.53 g of pure rac-dimethyl-bis-(2,5,5,7,7-pentamethyl-1,5,6,7-tetrahydro-s-indacen-1-yl)-silane (1.0 mmol) in 10 ml of diethyl ether at 0° C. After 90 min stirring at room temperature, the pale yellow suspension was added to a suspension of 0.25 g of $ZrCl_4$ (Aldrich, 1.1 mmol) in 10 ml of Pentane at 0° C. A yellow suspension was formed. After 20 hours stirring at room temperature $^1$H-NMR analysis showed the formation of the desired product (rac:meso=95:5,). The rac isomer was used for the polymerization tests.

Rac isomer $^1$H-NMR ($CDCl_3$, δ, ppm): 1.22, 1.31 (s, $CH_3$, H11, 12H); 1.28 (s, Si—$CH_3$, 6H); 1.33, 1.42 (s, $CH_3$, H10, 12H); 1.90 (d, $CH_2$, H6, 4H, J=0.78); 2.19 (s, $CH_3$, H9, 6H); 6.70 (s, CH, H3, 2H); 7.22 (s, Ar, H4, 2H, J=0.78); 7.28 (s, Ar, H8, 2H, J=0.78). $^{13}$C-NMR ($CD_2Cl_4$, δ, ppm): 2.86 (Si—$CH_3$, 2C); 18.39 ($CH_3$, C9, 2C); 31.41 ($CH_3$, C11, 2C); 31.63, 31.64 ($CH_3$, C10 e C11, 4C); 33.43 ($CH_3$, C10, 2C); 41.72, 41.75 (C, C5 e C7, 4C); 57.50 ($CH_2$, C6, 2C); 81.77 (Ar, C1, 2C); 117.77 (Ar, C8, 2C); 118.40 (Ar, C4, 2C); 121.37 (Ar, C3, 2C); 127.21 (Ar, C8a, 2C); 133.44 (Ar, C3a, 2C); 134.64 (Ar, C2, 2C); 152.15 (Ar, C7a, 2C); 155.45 (Ar, C4a, 2C).

Example 2

Alternative Route for the Synthesis of $Me_2Si$[2-Me-5,6(tetramethylcyclotrymethylen)indenyl]$_2$$ZrCl_2$[A1]

5.0 ml of a 2.5 M BuLi solution (Aldrich, 12.6 mmol) were slowly added to a suspension of 3.2 g of pure dimethyl-bis-(2,5,5,7,7-pentamethyl-1,5,6,7-tetrahydro-s-indacen-1-yl)-silane (experiment 20826/93, MW=508.86, 6.3 mmol) in 40 ml of ether at 0° C. After 3 hours stirring at room temperature, the pale yellow suspension was added to a suspension of 1.50 g of $ZrCl_4$ in 40 ml of Pentane at 0° C. A yellow-orange suspension was formed. After 18 hours stirring at room temperature $^1$H-NMR analysis showed the formation of the desired product (rac:meso=60:40,), so the suspension was filtered. The yellow residue (3.6 g) was treated on the frit with toluene (≈300 ml). The filtrate was evaporated to dryness under reduced pressure to give 2.41 g of a yellow powder containing $Me_2Si$[2-Me-5,6(tetramethyltrimethylen)indenyl]$_2$$ZrCl_2$ (rac:meso=61:39). The pale yellow residue on the frit was treated with 50 ml of toluene and filtered. 160 mg of pure rac-$Me_2Si$[2-Me-5,6(tetramethyltrimethylen)indenyl]$_2$ $ZrCl_2$ were obtained from the filtrate. The total yield was 61.2%. The rac isomer was used for the polymerization tests.

Polymerization Examples

General Procedures

The intrinsic viscosity (I.V.) was measured in tetrahydronaphtalene (THN) at 135° C.

The molecular weight and the molecular weight distribution were determined on a WATERS 150 C using the following chromatographic conditions:

| | |
|---|---|
| Columns: | 3x SHODEX AT 806 MS; 1x SHODEX UT 807; 1x SHODEX AT-G; |
| Solvent: | 1,2,4 trichlorobenzene (+0.025% 2,6-Di-tert.Butyl-4-Methyl-Phenol); |
| Flow rate: | 0.6–1 ml/min; |
| Temperature: | 135° C.; |
| Detector: | INFRARED AT $\lambda \cong 3.5$ μm; |
| Calibration: | Universal Calibration with PS-Standards. | constant, the catalytic solution was fed into the reactor with a nitrogen overpressure. The polymerisation was run for the time indicated in table 1 at the chosen polymerization temperature. Then the stirring was interrupted; the pressure into the autoclave was raised to 20 bar-g with nitrogen. The bottom discharge valve was opened and the 1-butene/poly-1-butene mixture was discharged into a heated steel tank containing water at 70° C. The tank heating was switched off and a flow of nitrogen at 0.5 bar-g was fed. After 1 hour cooling at room temperature the steel tank was opened and the wet polymer collected. The wet polymer was dried in an oven under reduced pressure at 70° C. The polymerization conditions and the characterization data of the obtained polymers were reported in Table 1.

TABLE 1

| Ex | met. (mg) | mmol Al | Al/Zr | T °C. | time min | yield g | Activity kg/ ($g_{met}$*h) | I.V. dL/g | $T_m(II)$ °C. | $\Delta H_f$ J/g | $M_w$ | $M_w/M_n$ |
|---|---|---|---|---|---|---|---|---|---|---|---|---|
| 1 | A-1 (3) | 4.42 | 990 | 50 | 60 | 110 | 37 | 1.99 | 97.3 | 27 | 715 600 | 2.4 |
| 2 | A-1 (3) | 4.42 | 990 | 70 | 60 | 310 | 103 | 1.44 | 92.7 | 27 | 356 300 | 2.1 |
| 3 | A-1 (3) | 4.42 | 990 | 80 | 60 | 144 | 48 | 1.23 | 92.5 | 26 | 244 600 | 2.2 |
| 4* | A-2 (4) | 6.29 | 990 | 70 | 60 | 50 | 12.5 | 0.81 | 102.3. | 28 | 152 500 | 2.5 |
| 5* | A-3 (7.4) | 13.6 | 1060 | 70 | 120 | 244 | 16.5 | 0.95 | 91.5 | 29.5 | 177 900 | 2.2 |

*comparative
n.a. = not available

The melting points of the polymers ($T_m$) were measured by Differential Scanning Calorimetry (D.S.C.) on a Perkin Elmer DSC-7 instrument, according to the standard method. A weighted sample (5–10 mg) obtained from the polymerization was sealed into aluminum pans and heated to 180° C. at 10° C./minute. The sample was kept at 180° C. for 5 minutes to allow a complete melting of all the crystallites, then cooled to 20° C. at 10° C./minute. After standing 2 minutes at 20° C., the sample was heated for the second time at 180° C. with a scanning speed corresponding to 10° C./min. In this second heating run, the peak temperature was taken as the melting temperature ($T_m$) and the area of the peak as melting enthalpy ($\Delta H_f$).

Rac dimethylsilylbis(2-methyl-4-phenyl-indenyl) zirconium dichloride [A-2] was prepared according to U.S. Pat. No. 5,786,432. Rac dimethylsilylbis(2-methyl-4,5benzo-indenyl)zirconium dichloride [A-3] was prepared according to U.S. Pat. No. 5,830,821.

Polymerization Examples 1–3 and Comparative Examples 4–5

1-butene homopolymerization

The catalyst mixture was prepared by dissolving the metallocene with the proper amount of the MAO solution in toluene (Al/Zr ratio reported in table 1), obtaining a solution which was stirred for 10 min at room temperature before being injected into the autoclave. A 4.25 litres steel autoclave, equipped with magnetically stirred anchor (stirring rate 550 rpm) and with a Flow Record & Control system (FRC) having maximum flow rate of 9000 g/hour for 1-butene, was purged with warm nitrogen (1.5 barg $N_2$, 700° C., 1 hour). 1-Butene was fed into the reactor (1350 g at 30° C.) together with 6 mmol of Al(i-Bu)$_3$ (TIBA) (as a 1 M solution in hexane), and stirring was started. Subsequently, the reactor inner temperature was raised from 30° C. to the polymerisation temperature (indicated in table 1). When pressure and temperature were

The invention claimed is:

1. A process for preparing 1-butene polymers optionally containing up to 30% by mol of derived units of ethylene, propylene or an alpha olefin of formula $CH_2=CHZ$, wherein Z is a $C_3$–$C_{10}$ alkyl group, comprising polymerizing 1-butene and optionally ethylene, propylene or said alpha olefin, in the presence of a catalyst system obtained by contacting:

a) at least a metallocene compound of formula (I):

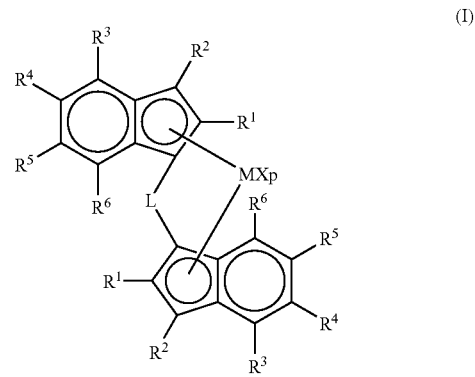

(I)

wherein:

M is an atom of a transition metal selected from those belonging to group 4;

p is 2, being equal to the formal oxidation state of the metal M minus 2;

X, equal to different from each other, are hydrogen atoms, halogen atoms, R, OR, $OSO_2CF_3$, OCOR, SR, $NR_2$ or $PR_2$ groups, wherein R is a linear or branched, $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radical, optionally containing heteroatoms belonging to groups 13–17 of the Periodic Table of the Elements;

R¹, equal to or different from each other, are linear or branched, $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radicals, optionally containing at least one heteroatom belonging to groups 13–17 of the Periodic Table of the Elements;

R², R³ and R⁶, equal to or different from each other, are hydrogen atoms or linear or branched, $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radicals, optionally containing at least one heteroatom belonging to groups 13–17 of the Periodic Table of the Elements;

R⁴ and R⁵, form together a condensed saturated or unsaturated $C_3$–$C_7$ membered ring optionally containing heteroatoms belonging to groups 13–16 of the Periodic Table of the Elements; every atom forming said ring being substituted with R⁷ radicals wherein R⁷, equal to or different from each other, are hydrogen atoms or linear or branched, $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radicals, optionally containing at least one heteroatom belonging to groups 13–17 of the Periodic Table of the Elements;

L is $Si(R^8)_2$ wherein R⁸ is a linear or branched, $C_1$–$C_{20}$ alkyl, $C_3$–$C_{20}$ cycloalkyl, $C_6$–$C_{20}$ aryl, $C_7$–$C_{20}$ alkylaryl, or $C_7$–$C_{20}$ arylalkyl radical; and b) an alumoxane or a compound that forms an alkylmetallocene cation.

2. The process according to claim 1 wherein the catalyst system further comprises an organo aluminum compound.

3. The process according to claim 1, wherein in the compound of formula (I), X is a halogen atom.

4. The process according to claim 1 wherein R¹ is a $C_1$-$C_{20}$-alkyl radical; R², R³ and R⁶ are hydrogen atoms and R⁷ is a hydrogen atom or a linear or branched, $C_1$-$C_{20}$-alkyl radical.

5. The process according to claim 1 wherein the compound of formula (I) has formula (IIa) or (IIb):

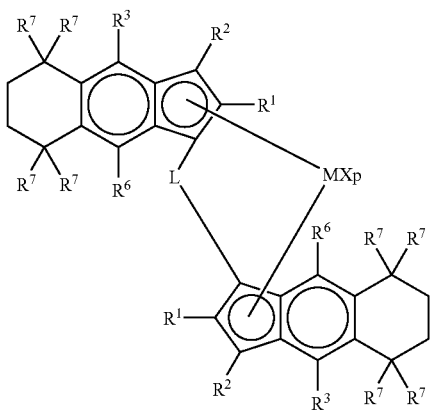

(IIa)

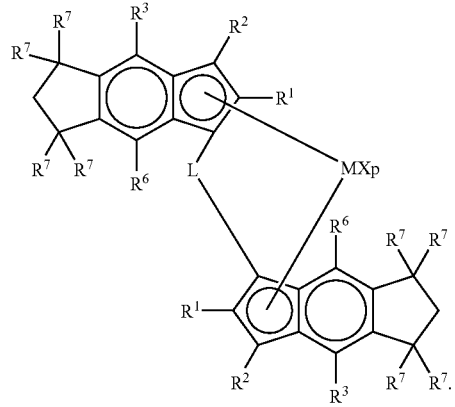

(IIb)

6. The process according to claim 5 wherein R⁷, equal to or different from each other, are linear or branched, $C_1$-$C_{20}$-alkyl, $C_3$-$C_{20}$-cycloalkyl, $C_6$-$C_{20}$-aryl, $C_7$-$C_{20}$-alkylaryl or $C_7$-$C_{20}$-arylalkyl radicals, optionally containing at least one heteroatom belonging to groups 13-17 of the Periodic Table of the Elements.

7. The process according to claim 6 wherein formula I is formula IIa.

8. The process according to claim 6 wherein formula I is formula IIb.

9. The process according to claim 1 wherein 1-butene is homopolymerized.

10. A metallocene compound of formula (IIb):

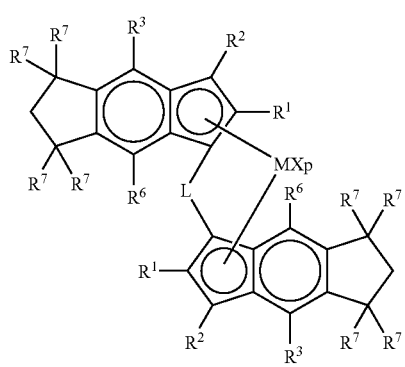

(IIb)

wherein

M is an atom of a transition metal selected from those belonging to group 4;

p is 2, being equal to the formal oxidation state of the metal M minus 2;

L is $Si(R^8)_2$ wherein R⁸ is a linear or branched, $C_1$–$C_{20}$ alkyl, $C_3$–$C_{20}$ cycloalkyl, $C_6$–$C_{20}$ aryl, $C_7$–$C_{20}$ alkylaryl, or $C_7$–$C_{20}$ arylalkyl radical;

R¹, equal to or different from each other, are linear or branched, $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radicals, optionally containing at least one heteroatom belonging to groups 13–17 of the Periodic Table of the Elements;

R², R³ and R⁶, equal to or different from each other, are hydrogen atoms or linear or branched, $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radicals, optionally containing at least one heteroatom belonging to groups 13–17 of the Periodic Table of the Elements;

$R^7$, equal to or different from each other, are linear or branched, $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radicals, optionally containing at least one heteroatom belonging to groups 13–17 of the Periodic Table of the Elements;

X, equal to different from each other, are hydrogen atoms, halogen atoms, R, OR, $OSO_2CF_3$, OCOR, SR, $NR_2$ or $PR_2$ groups, wherein R is a linear or branched, $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalky radical, optionally containing heteroatoms belonging to groups 13–17 of the Periodic Table of the Elements.

11. A process for preparing a metallocene compound of formula (IIb):

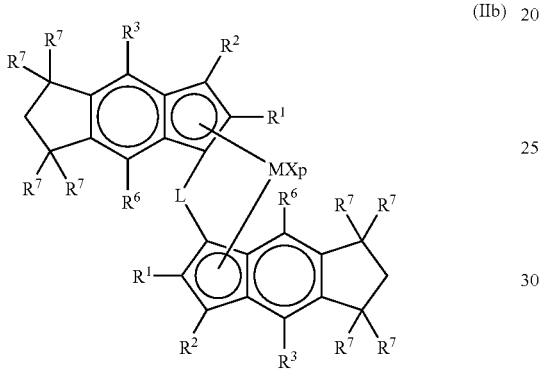

(IIb)

wherein

M is an atom of a transition metal selected from those belonging to group 4;

p is 2, being equal to the formal oxidation state of the metal M minus 2;

L is $Si(R^8)_2$ wherein $R^8$ is a linear or branched, $C_1$–$C_{20}$ alkyl, $C_3$–$C_{20}$ cycloalkyl, $C_6$–$C_{20}$ aryl, $C_7$–$C_{20}$ alkylaryl, or $C_7$–$C_{20}$ arylalkyl radical;

$R^1$, equal to or different from each other, are linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl optionally containing at least one heteroatom belonging to groups 13–17 of the Periodic Table of the Elements;

$R^2$, $R^3$ and $R^6$, equal to or different from each other, are hydrogen atoms or linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radicals, optionally containing one or more heteroatoms belonging to groups 13–17 of the Periodic Table of the Elements;

$R^7$, equal to or different from each other, are hydrogen atoms or linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radicals, optionally containing at least one heteroatom belonging to groups 13–17 of the Periodic Table of the Elements;

X, equal to different from each other, are halogen atoms, $OSO_2CF_3$ or OCOR groups, wherein R is a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl radical, optionally containing heteroatoms belonging to groups 13–17 of the Periodic Table of the Elements;

comprising the following steps:

a) contacting a ligand of formula (V):

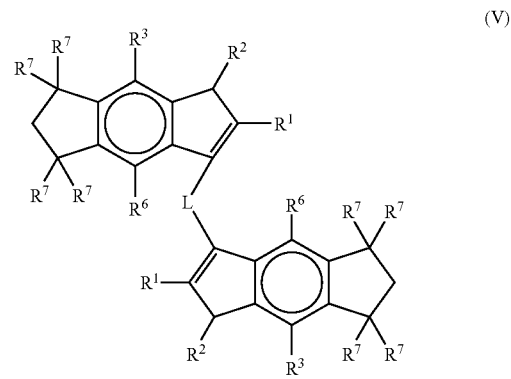

(V)

or its double bond isomer with a base of formula $T_jB$ or $TMgT^1$, or sodium or potassium hydride, or metallic sodium or potassium; wherein B is an alkali or alkaline earth metal and j is 1 or 2, j being equal to 1 when B is an alkaline metal, and j being equal to 2 when B is an alkali-earth metal; T is selected from the group consisting of linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl groups, optionally containing at least one Si or Ge atom; $T^1$ is a halogen atom or a group OR" wherein R" is a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl or $C_7$–$C_{20}$-arylalkyl radicals, optionally containing at least one heteroatom belonging to groups 13–17 of the Periodic Table of the Elements; wherein the molar ratio between said base and the ligand of the formula (V) and is at least 2:1; and b) contacting the product obtained in step a) with a compound of formula $MX_4$.

* * * * *